US012447052B2

(12) United States Patent
Hoggarth et al.

(10) Patent No.: US 12,447,052 B2
(45) Date of Patent: Oct. 21, 2025

(54) WOUND DRESSING

(71) Applicant: MEDTRADE PRODUCTS LIMITED, Crewe (GB)

(72) Inventors: Andrew Hoggarth, Crewe (GB); Ander Bugedo, Winsford (GB); Craig Hardy, Cardigan (GB)

(73) Assignee: MEDTRADE PRODUCTS LIMITED, Crewe (GB)

( * ) Notice: Subject to any disclaimer, the term of this patent is extended or adjusted under 35 U.S.C. 154(b) by 71 days.

(21) Appl. No.: 15/569,723

(22) PCT Filed: Apr. 25, 2016

(86) PCT No.: PCT/GB2016/051154

§ 371 (c)(1),
(2) Date: Oct. 26, 2017

(87) PCT Pub. No.: WO2016/174399

PCT Pub. Date: Nov. 3, 2016

(65) Prior Publication Data

US 2018/0125721 A1 May 10, 2018

(30) Foreign Application Priority Data

Apr. 27, 2015 (GB) ..................................... 1507132

(51) Int. Cl.
*A61F 13/0206* (2024.01)
*A61F 13/00* (2024.01)
(Continued)

(52) U.S. Cl.
CPC .... *A61F 13/0209* (2013.01); *A61F 13/00987* (2013.01); *A61F 13/01029* (2024.01); *A61F 13/022* (2013.01); *A61F 13/0276* (2013.01)

(58) Field of Classification Search
CPC ............ A61F 13/0206; A61F 13/00029; A61F 13/00987; A61F 13/0276; A61F 13/00042;
(Continued)

(56) References Cited

U.S. PATENT DOCUMENTS 5,763,331 A * 6/1998 Demhartner .......... A61F 13/534 442/393
2008/0312572 A1* 12/2008 Riesinger .......... A61F 13/00029 602/56

(Continued)

FOREIGN PATENT DOCUMENTS

EP 0617938 A1 10/1994
EP 0642779 A1 3/1995

(Continued)

OTHER PUBLICATIONS

International Search Report for Patent Application No. PCT/GB2016/051154 mailed on Sep. 7, 2016; 3 pages.

*Primary Examiner* — Jessica Arble
*Assistant Examiner* — Meagan Ngo
(74) *Attorney, Agent, or Firm* — Schwabe, Williamson & Wyatt, P.C.

(57) ABSTRACT

The present invention relates to a wound dressing composition for use as or in a wound dressing and to methods of making the wound dressing composition. The wound dressing composition comprises an absorbent material, an adhesive material and an anchor material attached to the absorbent material and the adhesive material. The anchor material is operable to maintain a link between the absorbent material and the adhesive material when the wound dressing composition is wet.

17 Claims, 3 Drawing Sheets

Figure 1:
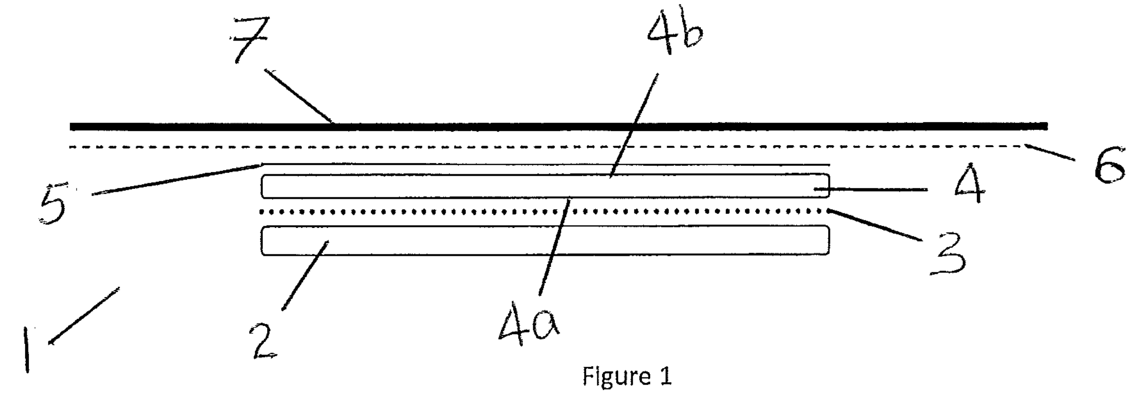

(51) Int. Cl.
*A61F 13/01* (2024.01)
*A61F 13/02* (2024.01)
*A61F 13/0203* (2024.01)

(58) Field of Classification Search
CPC ...... A61F 13/0209; A61F 2013/530481; A61F 13/022; A61F 13/00046; A61F 2013/00748
See application file for complete search history.

(56) References Cited

U.S. PATENT DOCUMENTS

| | | | | |
|---|---|---|---|---|
| 2009/0216168 | A1* | 8/2009 | Eckstein | A61L 15/26 602/43 |
| 2010/0010462 | A1 | 1/2010 | Kurata | |
| 2010/0069863 | A1* | 3/2010 | Olson | A61F 13/00987 604/368 |
| 2011/0110996 | A1* | 5/2011 | Schoenberger | A61L 15/26 424/401 |
| 2012/0095380 | A1* | 4/2012 | Gergely | A61F 13/0226 602/45 |
| 2012/0191056 | A1* | 7/2012 | Nozaki | A61F 13/534 604/372 |
| 2013/0165881 | A1* | 6/2013 | Boothman | A61F 13/0206 604/385.03 |
| 2013/0296818 | A1* | 11/2013 | Bradford | A61F 13/00987 604/368 |
| 2014/0058310 | A1 | 2/2014 | Pernot et al. | |
| 2015/0088085 | A1* | 3/2015 | Rovaniemi | A61F 13/0206 604/385.03 |
| 2016/0175156 | A1* | 6/2016 | Locke | A61F 13/00055 604/318 |
| 2016/0206483 | A1* | 7/2016 | Nishikawa | A61F 13/49017 |

FOREIGN PATENT DOCUMENTS

| | | | |
|---|---|---|---|
| EP | 2856987 | A1 | 4/2015 |
| KR | 20110056415 | A | 5/2011 |
| WO | 2008028337 | A1 | 3/2008 |
| WO | 2009008788 | A1 | 1/2009 |
| WO | 2010033574 | A1 | 3/2010 |
| WO | 102013002561 | A1 | 8/2014 |
| WO | 2015002934 | A2 | 1/2015 |
| WO | 2016174399 | A1 | 11/2016 |

* cited by examiner

WOUND DRESSING

CROSS REFERENCE TO RELATED APPLICATIONS

The present application is a national phase entry under 35 U.S.C. § 371 of International Application No. PCT/GB2016/051154, filed Apr. 25, 2016, entitled "WOUND DRESSING", which claims priority to GB Application No. 1507132.7 filed on Apr. 27, 2015, which are hereby incorporated by reference in their entireties.

The present invention relates to a wound dressing composition for use as, or in, a wound dressing, and also to methods of making the wound dressing composition.

Topical wound dressings for use in the treatment of wounds or other openings at a physiological target site on a human or animal body which are exuding blood and/or other bodily fluids have been known for some time. The materials used to make the wound dressings act to absorb the blood and/or other bodily fluids, and also stem the flow of them from the body. Materials for wound dressings are described in, for example, WO 2010/031995 and PCT/GB2015/050816 to MedTrade Products Limited, and are commercially available.

The management of exudate is of course essential and critical during wound care and surgical procedures. The aim of managing the exudate is essentially to provide a moist wound environment at the wound bed to minimise the risk of maceration, which in turn may reduce the negative impact upon the human or animal body and also shorten the length of time the patient will take to recover.

Wound dressings often comprise at least a quantity of an absorbent material. The purpose of the absorbent material is to absorb wound exudate from the wound, thereby drawing it away from the wound bed. This avoids the wound bed being overly wet which, as noted above, can be detrimental to the healing process.

In certain cases the absorbent material is either not bonded or is only loosely bonded to the wound contact layer, and upon contact with fluid, the absorbent material becomes free floating within the dressing. Such wound dressings therefore require the superabsorbent material to be contained in an envelope or a similar design in order to prevent the superabsorbent material from leaching or migrating into the wound or peri-wound area, and also to maintain dressing integrity, such that it can subsequently be removed in one piece.

To overcome this, superabsorbent fibre technologies, i.e. nonwoven materials, providing a greater tensile strength structure, can be used. Again, dependent on the bonding capability to other layers, these are often constructed as an envelope or a similar design.

As a simplistic overview, wound dressings manage wound exudate by three properties: fluid absorbency, fluid retention and moisture vapour transmission rates. Fluid absorbency is important to wick excess fluid from the wound bed, minimising the risk of maceration. Fluid retention post fluid absorbency is important in that it minimises the ability for fluid to migrate out of the dressing back into the wound bed or peri-wound area, again minimising the risk of wound and skin maceration. To try and minimise the dressing reaching maximum absorbency and to prolong usability of the dressing, moisture vapour transmission rates in the outer layer of the dressing are used, in essence allowing moisture to transfer to the atmosphere, and helping manage the fluid through the dressing. The combination of absorbency and moisture vapour transmission rates is termed total fluid handling.

In a wound dressing whereby the superabsorbent fibres are used in a textile form, when the superabsorbent material absorbs wound exudate, it typically expands and swells. In some instances, the superabsorbent material gels. This can cause an increase in rigidity of the dressing, making it uncomfortable to wear and potentially making it less conformable to the contours of a body part, whereby the dressing may come away from the skin. In order to maximise total fluid handling, dressings often have highly breathable backing materials. In such cases, the moisture loss from the superabsorbent fibre nonwoven layer may result in this layer drying out and becoming brittle. This results in the dressing being less conformable and potentially uncomfortable for the wearer. Utilising a non-breathable backing layer helps minimise the moisture loss and so slows down the drying of the superabsorbent fibre layer. It does however result in a lower total fluid handling capacity for the wound dressing, and potentially increases the risk of maceration or the need for dressing changes, demanding more healthcare support and costs.

There therefore remains a need for a composition suitable for use as, or in, a wound dressing that can address the aforementioned problems. The present invention has been arrived at with the foregoing in mind.

According to the present invention, there is therefore provided a wound dressing composition comprising a first layer of an absorbent material, a second layer of a superabsorbent polymer in the form of a powder or granules, and a third layer of a superabsorbent material in the form of fibres, wherein the second layer is positioned between the first layer and the third layer.

The presence of the superabsorbent polymer material between the first and second layers enables the third layer of the superabsorbent fibre material to maintain a desired moisture level, thus preventing it from drying out when the wound dressing composition is in use.

The wound dressing composition of the present invention maintains conformability and prevents excessive drying out when the composition is exposed to fluid, such as wound exudate. Thus, the wound dressing composition of the invention is beneficial in that wound exudate can be absorbed without the concern of the superabsorbent material making the dressing harden, reducing its conformability to the contours of a body part, and potentially causing it to delaminate from the skin. The combination of the superabsorbent polymer with the superabsorbent fibre materials maintains a level of moisture within the dressing such that the dressing remains conformable and comfortable. It also enables the level of absorbent fibre to be reduced whilst simultaneously maintaining the total fluid handling characteristics of the wound dressing.

The term 'wound' is used herein to refer to any breach or opening in the skin or subcutaneous tissue at a physiological target site of a human or animal. Typically, the present invention relates to a physiological target site of a human. The term physiological target site may also be referred to herein as a wound site.

The term 'wound dressing' is used herein to refer to materials placed on a wound at a wound site that have absorbent, gelling, adhesive or protective properties. The wound dressings are not limited to a particular size or shape. The wound dressings may be placed in direct or indirect contact with the wound. The wound dressings may comprise, or consist of, a wound dressing composition as defined herein.

The term 'absorbent material' is used herein to refer to a physiologically acceptable material that is capable of absorbing fluid, such as wound exudate, and which is capable of absorbing fluid to greater than about 500% by weight of the absorbent material, and with a fluid retention of greater than about 40%. The absorbent material referred to herein may also be a superabsorbent material. Reference to an absorbent material also includes reference to a superabsorbent material unless expressed otherwise.

The term 'superabsorbent material' is used herein to refer to a hydrophilic material that is water-swellable, but not water soluble, and which is capable of absorbing fluid to greater than about 2000% by weight of the superabsorbent material, preferably greater than about 2500%, with a fluid retention of greater than about 85%, preferably greater than about 90%.

The term 'superabsorbent polymer' is used herein to refer to a hydrophilic polymeric powder or granule that is a physical absorber and is water-swellable, but not water soluble, and which is capable of absorbing fluid to greater than about 2000% by weight of the superabsorbent polymer, preferably greater than about 2500%, with a fluid retention of greater than about 85%, preferably greater than about 90%.

The term 'water-swellable' is used herein to refer to a material that, when contacted with water or water-containing fluid, will absorb the fluid and swell, but will not substantially dissolve in that fluid. In some instances, at least a portion of the material will gel upon contact with water or a water-containing fluid.

The term 'water soluble' is used herein to refer to a material that, when contacted with water or a water-containing fluid, will readily dissolve in that fluid.

According to one embodiment of the invention, the absorbent material in the first layer may comprise, or consist of, a foam, such as a polymeric foam material, that is not a superabsorbent material. The polymeric foam may be a polyurethane foam.

The superabsorbent material in the third layer may comprise a material selected from starch, cellulose and polymeric materials such as poly(vinyl alcohol) (PVA), poly (ethylene oxide) (PEO), and poly(acrylic acid). The poly (acrylic acid) may be a partially neutralised, lightly cross-linked poly(acrylic acid). This material is in a fibrous form.

The superabsorbent material in the third layer may be chemically modified. For example, the superabsorbent material may be a polymeric material obtained by graft polymerisation of acrylic acid onto the chain of carboxymethyl cellulose.

Alternative superabsorbent materials include carboxymethylcellulose and chitosan fibre derivatives. For example, the chitosan fibre derivatives may comprise the materials described in WO 2010/031995, the contents of which are incorporated herein by reference. Thus, the superabsorbent material may comprise a blend of chitosan fibres with a material that has an acid associated therewith, e.g. cellulose fibre coated with an acid such as acetic and/or lactic acid.

Typically, the superabsorbent material is a partially neutralised, lightly cross-linked poly(acrylic acid).

The superabsorbent polymer (SAP) in the second layer may comprise, or consist of, a material selected from starch, cellulose and polymeric materials such as poly(vinyl alcohol) (PVA), poly(ethylene oxide) (PEO), and poly(acrylic acid). The poly(acrylic acid) may be a partially neutralised, lightly cross-linked poly(acrylic acid). They may comprise, or consist of, the following groups: synthetic produced SAPs from acrylic monomers, polysaccharide-based SAPs produced from carbohydrate polymers (including polysaccharides such as chitin, cellulose, starch, and natural gums, for example xanthan, guar and alginates) and poly(amino acid)-based SAPs comprising polypeptides as the main or part of their structure.

Typically, the SAP comprises, or consists of, poly(acrylic acid).

The superabsorbent polymer is provided in the form of a powder or granules. Typically, the powder or granules have an average particle size of between 100 to 800 μm By 'average particle size' is meant an average diameter of the powder or granule particles used as measured across their widest points.

The terms "cross-linking" or "cross-linked" are used herein to refer to two or more polymer chains being linked by a primary bond, such as a covalent bond.

The term "lightly cross-linked" is used herein to refer to embodiments wherein the number of cross-linking primary bonds in the superabsorbent material is less than the total number of possible cross-linking bonds.

The superabsorbent material is in the form of fibres. The fibres may be up to about 100 mm in length, preferably from about 5 to about 75 mm, more preferably from about 10 to about 60 mm and most preferably from about 30 to about 55 mm. Good results have been observed using fibres in the range of 38 to 52 mm in length.

The absorbent material in the first layer may be in the form of a woven or non-woven fibrous layer. Preferably, the absorbent material is in the form of a non-woven fibrous layer. Where the absorbent material is in the form of a layer, it will typically comprise a wound facing surface and non-wound facing surface.

The term "wound facing surface" is used herein to refer to a surface of a layer of material that, in use, faces toward the wound site. The term "non-wound facing surface" refers to a surface of a layer of material that, in use, faces away from the wound site.

The superabsorbent material and superabsorbent polymer in the third and second layers, respectively, may gel on contact with water or body fluid(s). The superabsorbent material may be a gelling or semi-gelling material.

The term 'gelling material' is used herein to refer to a material in which substantially all of the components therein may gel upon contact with water or body fluid(s). For example, it may comprise a fibrous material wherein substantially all of the fibres are capable of gelling upon contact with water or body fluid(s).

The term 'semi-gelling' is used herein to refer to a material that comprises a mixture of components, some of which gel upon contact with water or body fluid(s) and some of which do not. For example, a semi-gelling absorbent material may comprise a combination of fibres, some of which gel upon contact with water or body fluid(s) and some of which do not.

The term 'non-gelling' is used herein to refer to a material in which substantially all of the components therein do not gel upon contact with water or body fluid(s). For example, it may comprise a fibrous material wherein substantially all of the fibres are incapable of gelling upon contact with water or body fluid(s).

According to one embodiment, the superabsorbent polymer may be mixed with an adhesive material, in order to aid the bonding of the second layer to the first and third layers.

The adhesive material may consist of, or may comprise, any suitable physiologically acceptable adhesive.

The adhesive material may be a pressure sensitive adhesive, a heat-bonding adhesive, and the like. Typically, the adhesive material is a pressure sensitive adhesive. The adhesive material may be polymeric. Typically, the adhesive material is selected from acrylic adhesives, polyurethane adhesives, and silicone adhesives.

According to a further embodiment of the invention, on the side of the third layer of the superabsorbent material distal from the location of the wound, there may further comprise a layer of an anchor material.

In some embodiments, the anchor material may be attached to the adhesive material by contacting the anchor material with the adhesive material and applying pressure.

The adhesive material may be in the form of a layer. The adhesive layer comprises a wound facing surface and a non-wound facing surface.

The adhesive material may cover the whole or a part of a non-wound facing surface of the anchor material. The adhesive material may cover around 50-100% of the non-wound facing surface of the anchor material, preferably from around 70-80% coverage and most preferably around 75% coverage. In some embodiments, the adhesive material may cover substantially 100% of the non-wound facing surface of the anchor material. It is noted that, the higher the coverage of adhesive material, the stronger the bond between the adhesive material and the anchor material.

Where the adhesive material covers less than 100% of the non-wound facing surface of the anchor material, it may be located in intervals across such a surface. In such embodiments, the adhesive material may be located in regular or irregular intervals, preferably regular intervals.

The adhesive material may have a surface area greater than that of the anchor material and the absorbent material. In such embodiments, the adhesive material provides a border that outwardly extends beyond one or more edges of the anchor material and the absorbent material. Beneficially, the adhesive material provides a dual purpose of (a) providing an area of adhesive material to adhere to the anchor material and (b) providing a border around the adhered anchor material which can adhere to the skin surrounding the wound site. The adherence of the adhesive material to the skin of a patient can hold the wound dressing composition in place during use.

The anchor material is operable to maintain a link between the absorbent material and the adhesive material when the wound dressing composition is wet. This is important when the dressing design is not an envelope design.

Where the dressing is not an envelope design, the anchor material may consist of, or may comprise, a material that is not water soluble and/or water-swellable. The anchor material may have a lower absorbency than the superabsorbent material of the third layer. The anchor material may be non-absorbent or substantially non-absorbent. The anchor material may be non-gelling or substantially non-gelling.

Typically, the anchor material is in the form of fibres. The fibres can be of any desired diameter or length and can be formed into a textile fabric, a pad or a film for use.

The anchor material may be polymeric. Typically, the anchor material comprises polyethylene. Preferably, the polyethylene is high-density polyethylene (HDPE).

In alternative embodiments, the anchor material may be a textile, for example cotton and/or viscose. In such embodiments, the textile material would need to be attached to the absorbent material by needle punching.

Typically, the anchor material is in the form of a film or net. The film or net may comprise woven and/or non-woven fibres. Typically, the film or net comprises a woven structure. Such a woven structure comprises apertures. The apertures provide breathability to the anchor material and generally need to be large enough to allow the passage of fluid vapour therethrough. The aperture size is typically greater than about 0.2 $mm^2$, preferably from about 0.5 to about 1.0 mm. The anchor material may comprise from about 10 to about 100 apertures per $cm^2$, preferably from about 10 to about 50 apertures per $cm^2$, more preferably from about 15 to about 30 apertures per $cm^2$.

The breathability of the anchor material is preferably measured as grams per square meter (gsm) over 24 hours at 37° C. Typically, the breathability of the anchor material is greater than about 1500 gsm/24 hrs/37° C.

The anchor material may be in the form of a layer. The anchor layer comprises a wound facing surface and a non-wound facing surface. The anchor material may be referred to herein as a scrim or a net.

The thickness of the anchor material is typically from about 10 microns to about 200 microns, preferably from about 20 to about 100 microns, more preferably from about 30 to about 70 microns.

The weight of the anchor material is typically from about 10 to about 100 gsm, preferably from about 20 to about 80 gsm and more preferably from about 30 to about 70 gsm.

Typically, the anchor material is attached to a non-wound facing surface of the superabsorbent material in the third layer. The anchor material may cover the whole of the non-wound facing surface of the superabsorbent material. Alternatively, it may cover only a part of the non-wound facing surface. Preferably, the anchor material covers the whole of the non-wound facing surface.

The anchor material may be attached to the absorbent material by methods including heat-bonding, heat meltable adhesives and/or needle punching. Preferably, the absorbent material is heat-bonded to the anchor material.

The superabsorbent polymer in the second layer is presented within the construction of the wound dressing of the invention between the absorbent material and the superabsorbent material. Patent DE102013002561 (A1) teaches the making of pockets to contain the superabsorbent polymer powder. In this present invention, no pockets are required. The superabsorbent polymer may be contained between the two layers using heat-bonding, heat meltable adhesives and/or needle punching to bond the absorbent and superabsorbent layer. Preferably, the use of a heat meltable adhesive is used. When a heat meltable adhesive is used, the superabsorbent powder may be mixed with a dry heat meltable powder and scattered onto the surface of either the first or third layer.

A further patent US20040133176 A1, teaches the use of superabsorbent polymers for use in water conservation, agriculture and pollution control whereby the superabsorbent polymer is bonded to one side of a substrate such that the substrate has a structure creating sufficient free volume to permit said superabsorbent polymeric powder to expand upon contact with a liquid. In the case of this invention, the superabsorbent polymer is between two substrates to retain fluid to ensure the product does not dry out. Patent US20040133176 does not describe a layer that manages moisture vapour transmission rates. U.S. Pat. No. 6,972,011 B2 teaches the application of bonding a superabsorbent polymer to textile sheets using two layers of hot melt adhesives in between which sits the superabsorbent polymer.

In this present invention, the superabsorbent polymer is typically mixed with a hot melt adhesive powder creating a single layer and scattered onto a continuous belt driving the absorbent material through a heat lamination tunnel. The superabsorbent material layer is typically placed above the layer of superabsorbent/polymer mix prior to heating. A the end of the lamination heat tunnel, the construction can be cooled either by temperature or left at room temperature to cure and bond the layers together. There id sufficient superabsorbent material free within this structure to absorb fluid and expand.

In some embodiments, the ratio of superabsorbent polymer material to heat meltable adhesive is from about 50:1 to 1:50. The ratio of such materials may vary however, as it is dependent on the selection of wound contact material and its weight and thickness.

The wound dressing composition may additionally comprise further components of a wound dressing, such as for example, a backing material, and/or skin-contact or pressure sensitive adhesives.

The backing material is typically in the form of a layer, and, when present, represents the outermost layer, or the layer furthest away from the skin, of the wound dressing composition.

Beneficially, the backing material can act as a barrier to prevent contamination of the wound by contaminants such as bacteria. The backing material may also be waterproof.

The backing layer may be attached to the adhesive material by any appropriate means known to a person skilled in the art. Where the adhesive material comprises, or consists of, a pressure sensitive adhesive, the backing material can simply be contacted with the adhesive material and appropriate pressure applied. The backing material is preferably in the form of a film, more preferably a non-woven film.

The backing material may comprise, or consist of, a polymeric material, thin foams and fabrics. Typically, the backing material comprises, or consists of, polyurethane, polyethylene, and polyester. The polyester may be non-woven. Preferably, the backing material comprises, or is, polyurethane.

Suitable skin contact or pressure sensitive adhesives may include, but are not limited to, acrylate, silicone, or polyurethane based adhesives. They can be based on hydrogels and can be porous to moisture with a high moisture vapour transmission rate. They can be applied from water emulsions, solvents or using hot melt systems. The adhesives should have a good skin tack but give minimal skin trauma on removal. They can constitute 100% coverage of the backing, or a partial coverage thereof in the form of a pattern or mesh.

According to one embodiment, there is a layer of a skin contact or pressure sensitive adhesive on the non-wound contact side of the anchor material, and also a layer of a backing material thereon.

Suitable wound contact materials for use in the first layer of the wound dressing composition of the invention may include, but are not limited to, non-adherent layers which give very low or no adhesion to skin, wicking layers to speed-up the absorption of fluid, active carrier layers for delivery of a therapeutic material (such as a pharmaceutical, haemostat, antimicrobial, wound healing agent, or scar reducing agent) and adhesive layers to help in holding the dressing in place while potentially reducing trauma on removal. They can be based on a foam, polymer mesh, a fabric (e.g. nonwoven), and a hydrogel adhesive or partial adhesive coverings. The term "wound contact" is used herein to refer to a material that directly contacts the wound.

The wound contact material preferably provides a dual purpose of acting as a wicking layer to speed-up the absorption of fluid, such as wound exudate, whilst also preventing the leaching of absorbent material into the wound.

The wound contact material is preferably in the form of a foam. Typically, the wound contact material forms a layer. The wound contact layer comprises a wound facing surface and a non-wound facing surface. In some embodiments, the foam layer may have a thickness of from about 0.5 mm to about 7 mm, preferably from about 1.5 mm to about 3.0 mm.

Typically, the wound contact material is hydrophilic, such as a hydrophilic foam. The wound contact material may comprise, or consist of, a hydrophilic polymeric material. The term 'hydrophilic' is used herein to refer to a material that has an affinity with water. In the present invention, the hydrophilic wound contact material has an affinity for water, which enables it to readily absorb water containing wound fluid.

Typically, the wound contact material comprises, or consists of, polyurethane, polyethylene or a textile material. The polyurethane may be in the form or a foam or a perforated film. The polyethylene may be in the form of a foam. The textile material may be in the form of a net.

Preferably, the wound contact material comprises, or consists of, a polyurethane foam. Typically, the wound contact material consists of a polyurethane foam.

The wound contact material may cover the whole or a part of the wound facing surface of the absorbent material. Typically, the wound contact material covers the whole of the wound facing surface of the absorbent material.

As noted herein, the wound contact material preferably acts as a wicking layer. In use, the wound contact material will absorb wound fluid and thus draw it away from the wound bed. This has the advantageous effect of reducing the volume of fluid at the wound bed, thus avoiding a wound bed that is overly wet by creating a moisture level that is more conducive to wound healing. It is preferable to draw the wound fluid away from the wound contact material, as over saturation of the wound contact material results in an overly saturated wound bed. In the present invention, the wound contact material and the absorbent material can act in synergy, whereby the wound contact material initially readily absorbs fluid from the wound site and the absorbent material subsequently absorbs the fluid from the wound contact material. The superior retention properties of the absorbent material mean it can retain the wound fluid and keep it away from the wound bed. Beneficially, this can enhance the healing rate of the wound.

The wound dressing composition may further comprise a skin protection layer.

The skin protection layer may provide an alternative means of adhering the wound dressing composition to the skin surrounding the wound site. In such embodiments, the skin protection layer may be attached to the wound facing surface of the adhesive material that binds the anchor layer to the third layer. Preferably, the skin protection layer is attached to the wound facing surface of the border of the adhesive material, i.e. the part of the adhesive material that extends outwardly from the anchor material adhered thereto.

The skin protection layer contains an adhesive material for securing the dressing to the wound site, which may consist of a silicone material or pressure sensitive adhesive material. Silicone is ideally suited to application as the skin protection layer, since it can adhere to the skin in the same way as the adhesive material can, but it can be removed and reapplied with little irritation and damage. Also, the silicone material can be removed from the skin with reduced pain for the user compared to the adhesive material described herein.

The silicon layer may require a carrier material located between it and the adhesive material. The carrier material typically comprises a polymeric film. The carrier material may be the same material as the backing layer as described herein.

The skin protection layer adhered to the adhesive material may overlap with the non-wound facing surface of the anchor material. In such embodiments, the non-wound facing surface of the anchor material is attached to the adhesive material, as described herein, and is also attached to a part of the skin protection layer. This provides an increased stability for the wound dressing composition.

Alternatively, the skin protection layer may overlap with at least a part of the wound facing surface of the superabsorbent material of the third layer or the wound facing surface of the wound contact material of the first layer. Again, this provides increased stability to the wound dressing composition. It also provides a section of the skin protection layer that could be in direct contact with the wound site. Again, the gentle adherence of silicone material to the skin makes it ideally suited for contact with the wound site. Wounds and parts of wounds heal at different rates and stick to the wound dressing composition in different places and at different times. It is considered to be beneficial to have at least a part of the absorbent material, or the wound contact material if present, covered with a silicone material due to its gentle adherence to the wound site.

In some embodiments, the skin protection layer can extend across all or a part of the wound facing surface of the superabsorbent material of the third layer or the wound contact material of the first layer. In such embodiments, the skin protection layer is preferably perforated to facilitate absorption of the wound fluid by the wound contact material and/or the absorbent material whilst also providing a breathable composition and one that is gently adhered to the wound site.

According to a further aspect of the present invention, there is provided a wound dressing comprising a wound dressing composition as defined herein.

The wound dressing composition of the present invention, or a wound dressing comprising the wound dressing composition, may also comprise additional components mixed with any one or more of the material or layers described herein. Such additional components include, but are not limited to, pharmaceutical agents; wetting agents such as surfactants; growth factors; cytokines; agents which absorb agents which delay healing such as MMP's (matrix metalloproteinases) and elastase; and/or another wound dressing component, such as calcium, vitamin K, fibrinogen, thrombin, factor VII, factor VIII, clays such as kaolin, oxidised regenerated cellulose, gelatin, or collagen, etc.

Typical levels of any of these additional components could be from about 50 ppm up to about 50% by weight of the wound dressing composition. More typical levels would be less than 10%, still more typically less than about 5% by weight of the wound dressing composition. Additional components comprising less than about 1% by weight of the wound dressing composition are also envisaged by the present invention.

According to a further aspect of the present invention, there is provided a method of manufacturing a wound dressing composition as described herein, comprising the steps of:

(a) providing a first layer of an absorbent material, a second layer of a superabsorbent polymer in the form of a powder or granules, and a third layer of a superabsorbent material in the form of fibres; and
(b) attaching the second layer either to the first layer and to the third layer, either simultaneously or sequentially, whereby the second layer is positioned between the first layer and the third layer.

Typically, in step (b), the superabsorbent polymer is attached first to the first layer before it is attached to the third layer.

The method of the present invention may also typically comprise mixing the superabsorbent polymer in the form of a powder or granules with an adhesive material prior to step (b) above.

The method of the present invention may also comprise subsequently attaching an anchor layer and a backing layer, as defined herein above. These step(s) would be carried out after step (b) above.

The material and/or components of the wound dressing composition described herein may be provided in a sterile or non-sterile form. Where the materials and/or components are initially provided in a sterile form, sterilisation may be carried out using any of the methods conventionally known in the art, such as gamma irradiation, electron beam treatment, heat treatment, x-ray, etc., or it may alternatively be carried out by treatment using ethylene oxide. Sterilisation using ethylene oxide is preferred. A material in a non-sterile form may be provided in combination with one or more preservatives. However, it is preferred that the wound dressing composition is provided in a pre-sterilised form.

The wound dressing composition of the present invention, or wound dressing comprising such a wound dressing composition, is typically sterilised prior to packaging using any of the methods described herein. This enables the physician or emergency responder to use the wound dressing composition or wound dressing directly from the packaging, thus saving time.

According to a further aspect of the present invention, there is provided a use of a wound dressing composition as defined herein, or a wound dressing as define herein, in absorbing fluid discharged from a physiological target such as a wound, or in stemming a flow of a fluid discharged from a physiological target site.

According to a further aspect of the present invention, there is provided a wound dressing composition as defined herein, or a wound dressing as define herein, for use in absorbing fluid discharged from a physiological target such as a wound, or for use in stemming a flow of a fluid discharged from a physiological target site.

Figure 2:
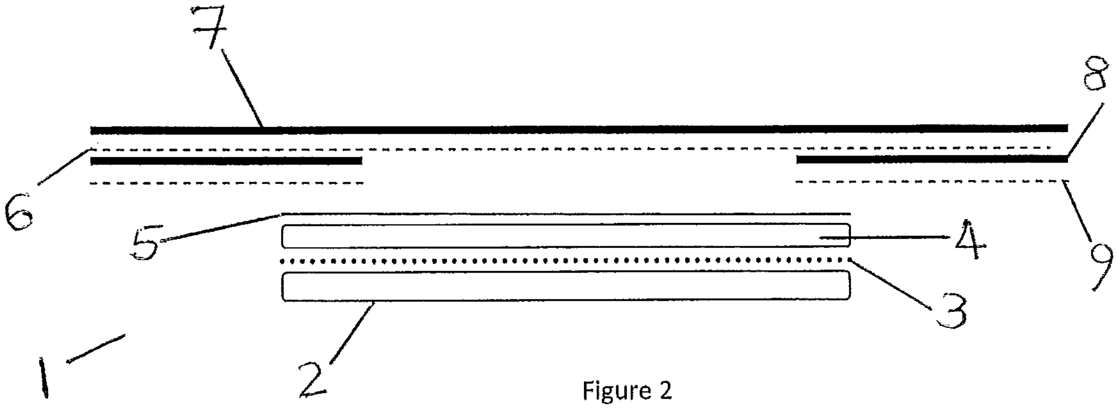
Figure 3:
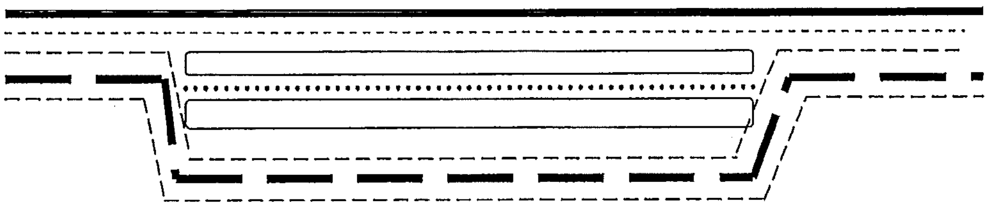
Figure 4:
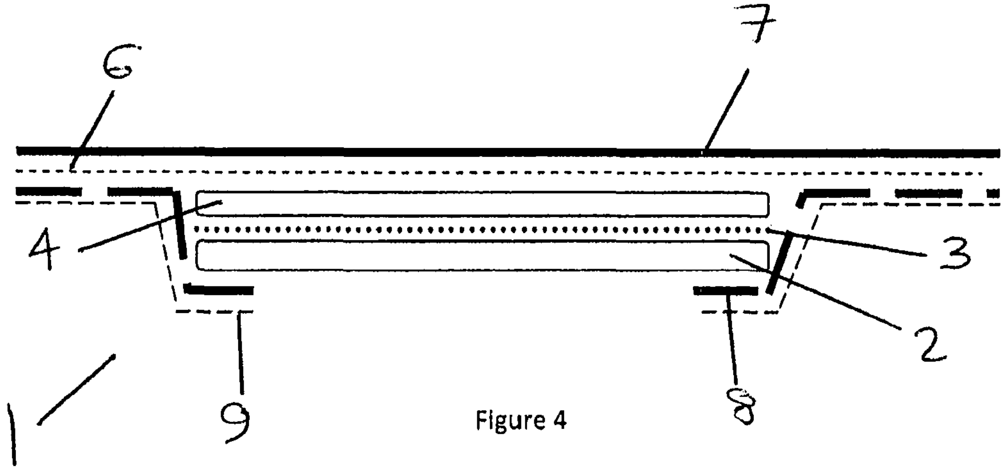
Figure 5:
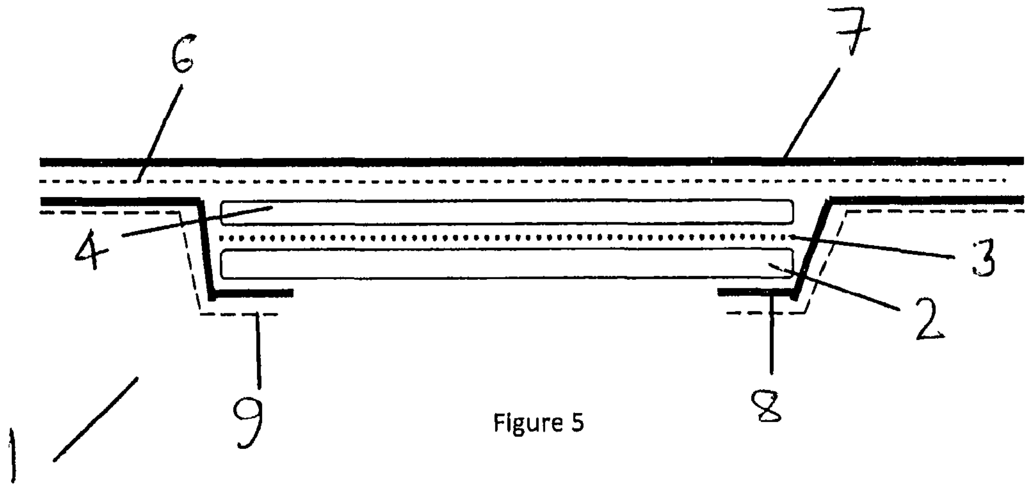
Figure 6:
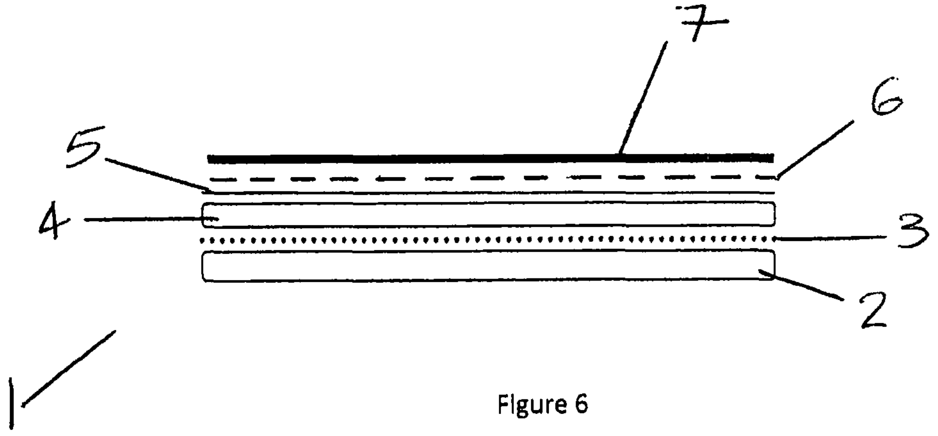
Figure 7:
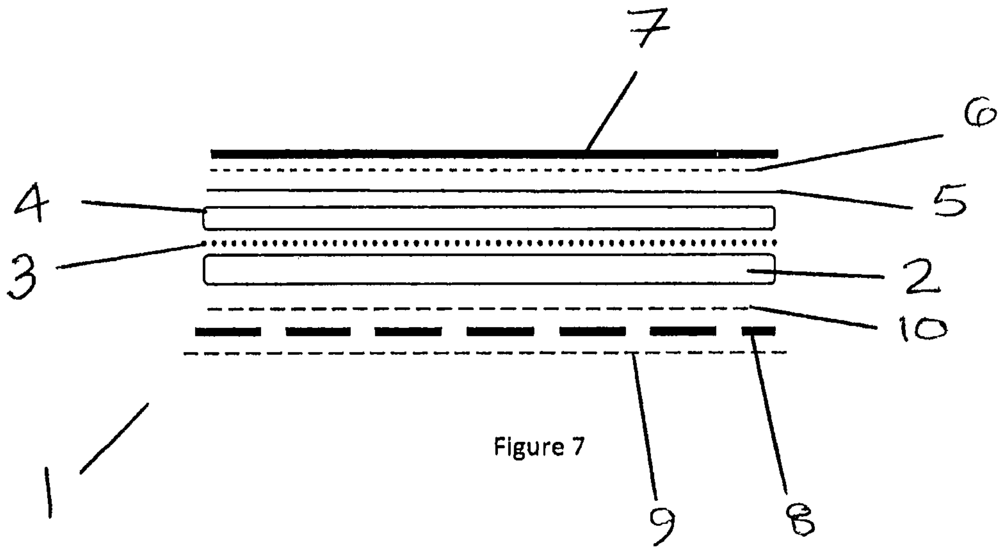

Embodiments of the present invention will now be further described with reference to the following non-limiting examples and accompanying figures in which:

FIG. 1: is a cross-sectional representation of a wound dressing composition according to an embodiment of the present invention;

FIG. 2: is a cross-sectional representation of an alternative wound dressing composition of the present invention;

FIG. 3: is a cross-sectional representation of a wound dressing composition of the present invention comprising a skin protection layer;

FIG. 4: is a cross-sectional representation of a further alternative wound dressing composition of the present invention comprising a skin protection layer;

FIG. 5: is a cross-sectional representation of a further alternative wound dressing composition of the present invention comprising a skin protection layer;

FIG. 6: is a cross-sectional representation of a further alternative wound dressing composition of the present invention;

FIG. 7: is a cross-sectional representation of the wound dressing composition of FIG. 6 further comprising a skin protection layer;

Referring to FIGS. 1 and 2, there is shown a wound dressing composition (1) comprising a layer of wound contact absorbent material as a first layer (2), a blend layer of superabsorbent polymer and meltable adhesive as a second layer (3), a layer of superabsorbent material as a third layer (4), a layer of anchor material (5), a layer of adhesive material (6), and a backing layer (7). FIG. 2 also has two layers around the border comprising of a carrier layer (8) and a skin friendly adhesive layer (9).

The wound contact absorbent material (2) is adjacent to the wound site and will come into direct contact with the wound upon application of the wound dressing composition (1) to a wound. The superabsorbent material (4) has a wound facing surface (4*a*) and a non-wound facing surface (4*b*). The wound contact absorbent material (2) is attached to the superabsorbent polymer (3) by a meltable adhesive. The wound contact absorbent layer (2) also serves to prevent or reduce the leaching of material from the blend layer of superabsorbent polymer, and meltable adhesive (3).

The superabsorbent polymer blended with the meltable adhesive (3) is positioned between the absorbent wound contact layer (2) and the superabsorbent material layer (4). In FIGS. 1 and 2, the bond created between these layers is such that it will not break when the respective materials get wet with wound fluid during use.

The anchor material (5) is attached to the non-wound facing surface (4*b*) of the superabsorbent material (4). Typically, the anchor material (5) is heat-bonded to the superabsorbent material (4). As described herein, the bond created between the anchor material (5) and the superabsorbent material (4) is such that it will not break when the respective materials get wet with wound fluid during use.

The adhesive layer (6) has a backing layer (7) attached to its non-wound facing surface. As with the anchor material (5), the backing layer (7) can be attached to the adhesive layer (6) by contacting the two materials together and applying pressure.

As can be seen in both FIGS. 1 and 2, the adhesive layer (6) and the backing layer (7) have a greater cross-sectional area than the anchor material (5), the superabsorbent material (4) and the wound contact material (2), creating a border portion (8). The wound facing surface of the backing layer (7) in the border portion (8) is, in use, applied directly to the patient's skin surrounding the wound site with the use of an adhesive (10). Thus, the adhesive layer (10) has the dual purpose of adhering to the anchor layer (5) and the skin of the patient.

FIG. 3 is an alternative design, whereby a perforated layer, comprising of a carrier layer (8), a layer of a pressure sensitive adhesive (10) proximal to the superabsorbent layer and a silicone adhesive layer proximal to the wound is used to envelope the fluid absorbing portion of the dressing. In doing so there is no requirement for the anchor layer. FIGS. 4 and 5 are alternatives to the embodiments in FIGS. 1 and 2, whereby the adhesive portion of the dressing that is used to secure it to the skin or wound of a person overlaps the wound contact layer, but not fully across this layer. This layer can be perforated or non-perforated.

FIGS. 6 and 7 each show a non-bordered version with and without an adhesive face. In using the combination of the superabsorbent polymer, absorbent layer and superabsorbent material, this reduces the risk of superabsorbent polymer leaching from the wound dressing edges.

In use, the wound dressing composition (1) of the present invention is applied to a wound by contacting the wound contact layer and/or the silicone layer with the wound site. The wound dressing composition (1) can be affixed to the patient's skin by applying downward pressure to the border portion or the non-bordered part where no border is present, or by means of a secondary securement device. Wound exudates from the wound will be absorbed by the absorbent wound contact layer (2) and drawn through to the superabsorbent layers (3, 4). This has the effect of drawing fluid away from the wound bed, creating a moisture level at the wound bed that is more conducive to healing.

EXAMPLES

The wound dressing compositions of the present invention do not delaminate, maintain a level of moisture and do not harden when the composition is exposed to fluid, such as wound exudate and then allowed to dry. To test this, the following experiment was followed.

Test Methodology

An island wound dressing as shown in FIG. 3 was prepared. The wound dressing was made up of a superabsorbent layer of polyacrylate fibres gsm 200, an a pattern coated adhesive layer of a pressure-sensitive acrylic adhesive 20 gsm, a backing layer of a highly breathable polyurethane film, 30 micron thickness and an absorbent wound contact layer of a polyurethane foam, 1.5 mm thickness and a superabsorbent polymer/dry hot meltable adhesive layer at 0.49 g per 100 $cm^2$. A second dressing was constructed as the control made up of a superabsorbent layer of polyacrylate fibres gsm 250, an a pattern coated adhesive layer of a pressure-sensitive acrylic adhesive 20 gsm, a backing layer of a highly breathable polyurethane film, 30 micron thickness and an absorbent wound contact layer of a polyurethane foam, 1.5 mm thickness and a dry hot meltable adhesive layer at 0.49 g per 100 $cm^2$.

Three wound dressings had the central absorbent pad area semi-saturated with solution A to half their absorbency potential. The absorbency potential was comparable for both dressing types. The dressings were then subjected to an incubator at 37° C. and assessed at different time intervals.

In the tests, Solution A is 142 mmol sodium ions and 2.5 mmol calcium ions as the chloride salt, Solution B is saline and Solution C is simulated wound fluid (50% peptone water and 50% fetal bovine serum).

The wound dressings were then inspected for softness and conformability. After 24 hrs the dressing with no superabsorbent polymer had lost some of its conformability and had dry hard sections within the central absorbent pad. This was not observed for the invention dressing. After 48 hrs, the dressing with no superabsorbent polymer has lost most of its conformability and felt very rigid and hard to the touch. This dressing did not arch under its own weight. The invention dressing still felt soft and confirmable and arch under its own weight. After 7 days, the invention dressing still maintained its conformability.

Further testing on fluid handling using the BS EN 13726-1:2002 test methodology gave the following results:

| | Full Dressing Absorption (g) | Total Fluid Handling (g/10 cm2/24 hr) | MVTR (g/10 cm2/ 24 hr) | Fluid absorbed (g/10 cm2/ 24 hr) |
|---|---|---|---|---|
| Control dressing | 28 | 8.8 | 6.2 | 2.5 |
| Invention | 29 | 8.0 | 4.0 | 4.1 |

The above result show comparable absorbency and total fluid handling results for the two dressings, the control and the invention. The use of the superabsorbent polymers retains more fluid within the dressing structure of the invention, reducing the breathability and as such minimising the risk of drying out.

It is of course to be understood that the present invention is not intended to be restricted to the foregoing examples which are described by way of example only.

The invention claimed is:

1. A wound dressing composition comprising:

a first layer of an absorbent material, wherein the absorbent material comprises a foam configured to directly contact a wound, a second layer of a superabsorbent polymer in the form of a powder or granules, wherein the superabsorbent polymer is mixed with an adhesive material, and a third layer of a superabsorbent material, wherein the superabsorbent material in the third layer is in the form of fibres comprising a material selected from starch, poly(vinyl alcohol), poly(ethylene oxide), poly(acrylic acid), a polymeric material obtained by graft polymerisation of acrylic acid onto a chain of carboxymethyl cellulose, and a blend of chitosan fibres with a material that has an acid associated therewith, or a derivative of any of the above, wherein the second layer is positioned between the first layer and the third layer and bonds the first layer of the absorbent material and the third layer of the superabsorbent material together.

2. The wound dressing composition according to claim 1, wherein the superabsorbent material in the third layer comprises poly(acrylic acid) or a derivative thereof.

3. The wound dressing composition according to claim 1, wherein the superabsorbent polymer is mixed with a hot meltable adhesive to bond the first layer of the absorbent material and the third layer of the superabsorbent material together.

4. The wound dressing composition according to claim 3, wherein the hot meltable adhesive comprises a pressure-sensitive adhesive.

5. The wound dressing composition according to claim 3, wherein the hot meltable adhesive is selected from acrylic adhesives and polyurethane adhesives.

6. The wound dressing composition according to claim 1, wherein the fibres form a non-woven layer.

7. The wound dressing composition according to claim 1, further comprising a backing layer that is highly breathable.

8. A method of absorbing fluid discharged from a physiological target, or in stemming a flow of a fluid discharged from a physiological target site, the method comprising use of the wound dressing composition according to claim 1.

9. The wound dressing composition according to claim 1, wherein the second layer comprises a cured mixture of the superabsorbent polymer and the adhesive material.

10. The wound dressing composition according to claim 9, wherein the adhesive material is in the form of a hot melt adhesive powder.

11. The wound dressing composition according to claim 1, wherein the third layer is gelling or semi-gelling upon contact with water or body fluid(s).

12. A method of manufacturing a wound dressing composition according to claim 1, comprising the steps of:

(a) providing a first layer of an absorbent material wherein the absorbent material comprises a foam configured to directly contact a wound, a second layer of a superabsorbent polymer in the form of a powder or granules, wherein the superabsorbent polymer is mixed with an adhesive material, and a third layer of a superabsorbent material, wherein the superabsorbent material is in the form of fibres comprising a material selected from starch, poly(vinyl alcohol), poly(ethylene oxide), poly (acrylic acid), a polymeric material obtained by graft polymerisation of acrylic acid onto the chain of carboxymethyl cellulose, and a blend of chitosan fibres with a material that has an acid associated therewith, or a derivative of any of the above; and (b) attaching the second layer either to the first layer or to the third layer, either simultaneously or sequentially, whereby the second layer is positioned between the first layer and the third layer.

13. The method according to claim 12, wherein the second layer is attached to the first layer before it is attached to the third layer.

14. The method according to claim 12, wherein the superabsorbent polymer is blended with an adhesive material prior to carrying out step (b).

15. The method according to claim 12, further comprising placing the third layer of the superabsorbent material layer above the second layer of superabsorbent polymer prior to heating and subsequent cooling, wherein the cooling cures the second layer and bonds the first layer of the absorbent material and the third layer of the superabsorbent material together.

16. A wound dressing comprising a wound dressing composition, the wound dressing composition comprising a first layer of an absorbent material wherein the absorbent material comprises a foam configured to directly contact a wound, a second layer of a superabsorbent polymer in the form of a powder or granules, and a third layer of a superabsorbent material, wherein the superabsorbent material is in the form of fibres comprising a material selected from starch, poly(vinyl alcohol), poly(ethylene oxide), poly (acrylic acid), a polymeric material obtained by graft polymerisation of acrylic acid onto a chain of carboxymethyl cellulose, and a blend of chitosan fibres with a material that has an acid associated therewith, or a derivative of any of the above, wherein the second layer is positioned between the first layer and the third layer and bonds the first layer of the absorbent material and the third layer of the superabsorbent material together.

17. A method of absorbing fluid discharged from a physiological target, or in stemming a flow of a fluid discharged from a physiological target site, the method comprising use of the wound dressing according to claim 16.

* * * * *